(12) United States Patent
Bartosz et al.

(10) Patent No.: US 11,584,540 B2
(45) Date of Patent: Feb. 21, 2023

(54) AIR QUALITY SENSORS AND METHODS OF MONITORING AIR QUALITY

(71) Applicant: Hamilton Sundstrand Corporation, Charlotte, NC (US)

(72) Inventors: Lance R. Bartosz, Granby, MA (US); Kenneth Carney, Rancho Cucamonga, CA (US); Hsien-chi W. Niu, Rowland Heights, CA (US); Catherine Thibaud, Cork (IE)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 992 days.

(21) Appl. No.: 16/376,506

(22) Filed: Apr. 5, 2019

(65) Prior Publication Data
US 2020/0317368 A1    Oct. 8, 2020

(51) Int. Cl.
*B65D 45/00* (2006.01)
*B64D 45/00* (2006.01)
(Continued)

(52) U.S. Cl.
CPC ............. *B64D 45/00* (2013.01); *B64D 13/06* (2013.01); *B64F 5/60* (2017.01); *G01N 27/04* (2013.01);
(Continued)

(58) Field of Classification Search
CPC ............. B64D 45/00; B64D 13/06; B64D 2013/0603; B64F 5/60; G01N 27/04;
(Continued)

(56) References Cited

U.S. PATENT DOCUMENTS 6,170,318 B1 *    1/2001    Lewis ............... G01N 33/497
                                                        422/98
2006/0257287 A1    11/2006    Call et al.
(Continued)

FOREIGN PATENT DOCUMENTS

EP        2808675 A1    12/2014
WO    2003089915 A1    10/2003
(Continued)

OTHER PUBLICATIONS

Extended European Search Report; Application No. 19209962.0; dated Jun. 8, 2020; 8 pages.

*Primary Examiner* — Robert R Raevis
(74) *Attorney, Agent, or Firm* — Cantor Colburn LLP (57) ABSTRACT

An air quality sensor includes a detector element array, a processor operatively connected to the detector element array, and a memory. The memory is disposed in communication with the processor and has instructions recorded on the memory that, when read by the processor, cause the processor to execute certain operations including measuring electrical resistance of one of more detector element of the detector element array. A difference is calculated between the measured resistance and a reference resistance, and a determination is made of presence or absence of a contaminant in air communicated to the detector element array from an atmosphere of an aircraft cabin based on the difference between the measured resistance and the reference resistance. Aircraft and methods of monitoring air quality also described.

11 Claims, 4 Drawing Sheets

(51) Int. Cl.
  *B64F 5/60* (2017.01)
  *B64D 13/06* (2006.01)
  *G01N 27/04* (2006.01)
  *G01N 33/00* (2006.01)
  *G07C 5/00* (2006.01)

(52) U.S. Cl.
  CPC .......... *G01N 33/0027* (2013.01); *G07C 5/00* (2013.01); *B64D 2013/0603* (2013.01)

(58) Field of Classification Search
  CPC ........... G01N 33/0027; G01N 33/0004; G01N 33/0057; G01N 33/0031; G01N 33/0032; G07C 5/00
  USPC .................. 702/24, 104; 340/945, 963, 971, 340/632–634; 73/1.02, 1.06, 31.01, 73/31.02, 31.03, 31.05, 865.8
  See application file for complete search history.

(56) References Cited

U.S. PATENT DOCUMENTS

| | | |
|---|---|---|
| 2008/0101434 A1 | 5/2008 | Horovitz et al. |
| 2018/0118351 A1 | 5/2018 | Fox et al. |
| 2018/0188166 A1 | 7/2018 | Zeller et al. |

FOREIGN PATENT DOCUMENTS

| | | |
|---|---|---|
| WO | 2016189420 A1 | 12/2016 |
| WO | 2018222789 A1 | 12/2018 |

* cited by examiner

AIR QUALITY SENSORS AND METHODS OF MONITORING AIR QUALITY

BACKGROUND

The subject matter disclosed herein generally relates to environmental control, and more particularly to monitoring air quality in controlled environments such as in aircraft cabins.

Aircraft cabin air is generally not monitored for the presence of contaminants. In some aircraft it can be necessary to monitor cabin air for the presence of contaminants, such as engine exhaust introduced to the cabin environment through the aircraft air supply system. On rare occasions a system malfunction may result in fumes and/or odors being introduced into the aircraft cabin air. On such occasions it is typically not possible to discriminate between fumes and odors associated with hazardous condition from fumes and odors associated with nuisance conditions.

Such systems and methods have generally been considered suitable for their intended purpose. However, there remains a systems and methods for monitoring environmental conditions within aircraft spaces. The present disclosure provides a solution to these needs.

BRIEF SUMMARY

In an embodiment an air quality sensor is provided. The air quality sensor includes a detector element array, a processor operatively connected to the detector element array, and a memory. The memory is disposed in communication with the processor and has instructions recorded thereon that, when read by the processor, cause the processor to (1) measure electrical resistance of one of more detector element of the detector element array; (2) calculate difference between the measured resistance and a reference resistance, and (3) determine presence or absence of a contaminant in air communicated to the detector element array from an atmosphere of an aircraft cabin based on the difference between the measured resistance and the reference resistance.

In addition to one or more of the features described above, or as an alternative, further embodiments may include wherein the instructions further cause the processor to quantify an amount of the contaminant in the air communicated to the detector element array.

In addition to one or more of the features described above, or as an alternative, further embodiments may include wherein the instructions further cause the processor to identify the contaminant based on the difference between the measured resistance and the reference resistance.

In addition to one or more of the features described above, or as an alternative, further embodiments may include wherein the instructions further cause the processor to distinguish the contaminant between a hazardous contaminant and a nuisance contaminant.

In addition to one or more of the features described above, or as an alternative, further embodiments may include a user interface operatively associated with the processor, wherein the instructions cause the processor to provide a countermeasure required signal to the user interface.

In addition to one or more of the features described above, or as an alternative, further embodiments may include a user interface operatively associated with the processor, wherein the instructions cause the processor to provide a no countermeasure required signal to the user interface.

In addition to one or more of the features described above, or as an alternative, further embodiments may include an enclosure with an interior, wherein the detector element array is arranged within the interior of the enclosure.

In addition to one or more of the features described above, or as an alternative, further embodiments may include a portable form factor.

In addition to one or more of the features described above, or as an alternative, further embodiments may include wherein the enclosure has a cabin-mountable form factor for fixation of the air quality sensor within a cabin of an aircraft.

In addition to one or more of the features described above, or as an alternative, further embodiments may include a first detector element having a first chemiresistive coating and a second detector element having a second chemiresistive coating.

In addition to one or more of the features described above, or as an alternative, further embodiments may include wherein at least one of the first chemiresistive coating and the second chemiresistive coating catalyze in the presence of a hazardous contaminant.

In addition to one or more of the features described above, or as an alternative, further embodiments may include wherein at least one of the first chemiresistive coating and the second chemiresistive coating catalyze in the presence of a nuisance contaminant.

In addition to one or more of the features described above, or as an alternative, further embodiments may include an enclosure with an inlet and an interior, a printed circuit board (PCB) arranged within the interior of the enclosure and supporting the detector element array, and an electrical erasable programmable read only memory (EEPROM) arranged within the interior of the enclosure and supported by the PCB. The PCB connects the processor to the memory, the EEPROM, and the processor for determining presence or absence of contaminant with real-time measurements of resistivity change of detector elements of the detector element array.

An aircraft is also provided. The aircraft includes a cabin containing an atmosphere. and an air quality sensor as described above. The air quality sensor is in fluid communication with the atmosphere contained within the cabin.

A method is additionally provided. The method includes communicating air from an atmosphere contained within a cabin of an aircraft to a detector element array; measuring resistance of a detector element of the detector element array; calculating difference between the measured resistance and a reference resistance; and determining presence or absence of a contaminant in the cabin based on difference between the measured resistance and the reference resistance.

In addition to one or more of the features described above, or as an alternative, further embodiments may include identifying the contaminant using the measured resistance of the detector element.

In addition to one or more of the features described above, or as an alternative, further embodiments may include reporting presence of a nuisance contaminant in the air when the contaminant is a nuisance contaminant, and reporting presence of a hazardous contaminant in the air when the contaminant is a hazardous contaminant.

In addition to one or more of the features described above, or as an alternative, further embodiments may include further comprising quantifying concentration of the contaminant using the measured resistance of the detector element.

In addition to one or more of the features described above, or as an alternative, further embodiments may include identifying the contaminant as one of a nuisance contaminant and a hazardous contaminant, executing a countermeasure when the contaminant is identified as a hazardous contaminant, and executing no countermeasure when the contaminant is identified as a nuisance contaminant.

In addition to one or more of the features described above, or as an alternative, further embodiments may include wherein the detector element is a first detector element, wherein the measured resistance is a first resistance, and wherein the reference resistance is a first resistance, the method further including measuring resistance of a second detector element of the detector element array, calculating difference between the measured resistance of the second detector element and a second reference resistance, and negating a determination of presence of the contaminant based on the difference between the first measured resistance and the first reference resistance.

Technical effects of embodiments of the present disclosure include the capability to discriminate between the presence of hazardous compounds and nuisance compounds in contaminants disposed within the atmosphere of an aircraft cabin. In certain embodiments the present provides the capability of aircrew to respond to the presence of hazardous and nuisance compounds in contaminants disposed within the atmosphere of an aircraft cabin. It is also contemplated that, in accordance with certain embodiments, the present disclosure provide the capability to retrofit and/or upgrade legacy aircraft and aircraft environmental control systems with the capability to monitor the atmosphere of an aircraft cabin for the presence of hazardous and nuisance compounds in atmosphere contaminants.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
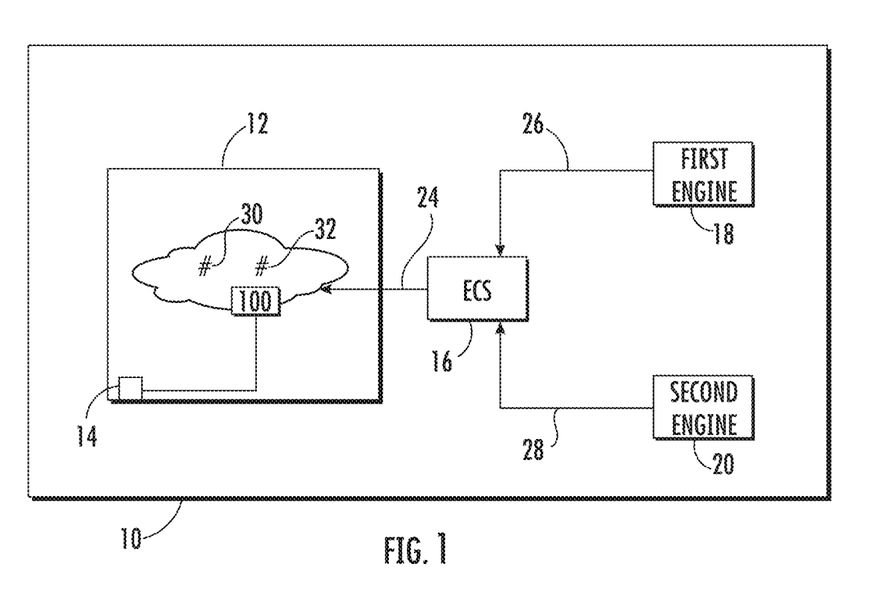
FIG. 1 is a schematic diagram of an air quality sensor constructed in accordance with the present disclosure, showing the air quality sensor disposed within the atmosphere contained within an aircraft cabin and monitoring the atmosphere for contaminants.

Reference will now be made to the drawings wherein like reference numerals identify similar structural features or aspects of the subject disclosure. For purposes of explanation and illustration, and not limitation, a partial view of an exemplary embodiment of an air quality sensor for monitoring an atmosphere for the presence of compounds indicative of contamination in accordance with the disclosure is shown in FIG. 1 and is designated generally by reference character 100. Other embodiments of air quality sensors, aircraft, and methods of monitoring air quality in accordance with the present disclosure, or aspects thereof, are provided in FIGS. 2-4, as will be described. The systems and methods described herein can be used for monitoring air quality in vehicles, such as in aircrafts, though the present disclosure in not limited to aircraft or to vehicles in general.

Referring to FIG. 1, an aircraft 10 is shown. The aircraft 10 includes a cabin 12, a 28-volt direct current (DC) power source 14, and an environmental control system (ECS) 16. The aircraft 10 also includes a first engine 18, a second engine 20, and the air quality sensor 100.

The cabin 12 contains an atmosphere 22. The atmosphere 22 is maintained using conditioned air 24 provided by the ECS 16. The ECS 16 is in turn provided with a supply of makeup air 26 from the first engine 18 and/or makeup air 28 the second engine 20. In certain embodiments the supply of makeup air 26 provided to the ECS 16 is bleed air provided by the at least one of the first engine 18 and the second engine 20. In accordance with certain embodiments, one the first engine 18 and the second engine 20 may be include a gas turbine engine, such as a main engine and/or an auxiliary power unit.

As will be appreciated by those of skill in the art in view of the present disclosure, contaminants can be introduced into an atmosphere contained within an aircraft cabin, e.g., the atmosphere 22 contained within the cabin 12. For example, in certain circumstances one or more hazardous contaminant 32 can be introduced into the atmosphere 22. As used herein the term "hazardous" refers a contaminant the presence of which warrants execution of a countermeasure, such as switching the source of the supply of makeup air 26 from one of the first engine 18 and the second engine 20 to the other of the first engine 18 and the second engine 20. Examples of hazardous contaminants include compounds attributed with system malfunctions, such as fire and/or smoke. In some circumstances one or more nuisance contaminant 30 can be introduced into the atmosphere 22. A used in herein the term "nuisance" refers to a contaminant the presence of which does not warrant execution of a countermeasure. Examples of nuisance contaminants include contaminants with tobacco smoke odors and fumes. To monitor the atmosphere 22 for the presence of contaminants generally, and in certain embodiments to distinguish between hazardous contaminants and nuisance contaminants within the atmosphere 22, the air quality sensor 100 is provided.

Figure 2:
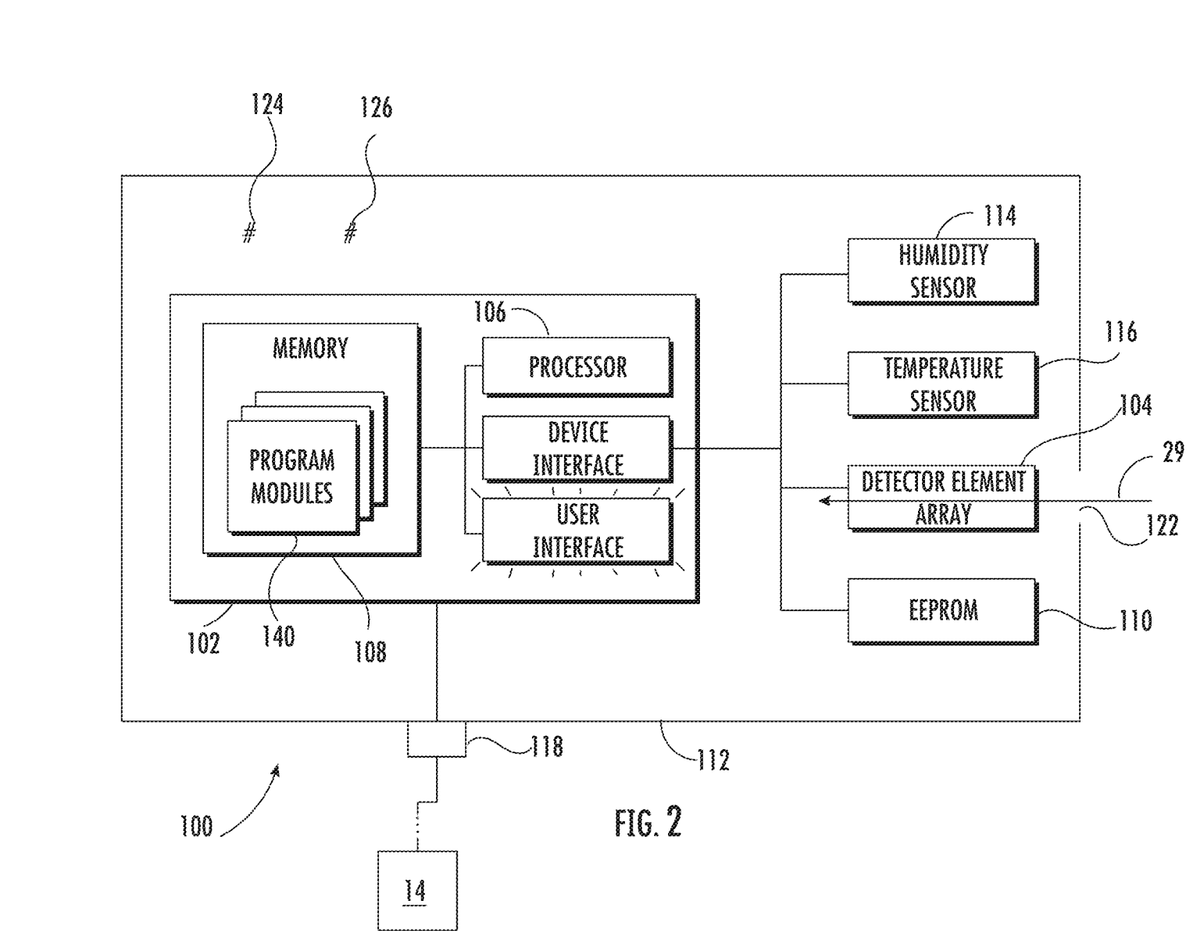
FIG. 2 is a schematic diagram of the air quality sensor of FIG. 1, showing a detector element array of the air quality sensor operatively associated with a processor and disposed in fluid communication with the atmosphere contained within the cabin.

With reference to FIG. 2, the air quality sensor 100 is shown. The air quality sensor 100 includes a printed circuit board (PCB) 102, a detector element array 104, and processor 106. The air quality sensor 100 also includes a memory 108, an electrically erasable programmable read-only memory (EEPROM) 110, and an enclosure 112. In certain embodiments the air quality sensor 100 additionally includes a relative humidity sensor 114, a temperature sensor 116, and a 28-volt connector 118.

The 28-volt connector 118 is fixed to the enclosure 112 and is connected to the PCB 102 to provide external power to the air quality sensor 100. It is contemplated that the 28-volt connector 118 provide electrical power to the air quality sensor 100 from the 28-volt DC power source 14 when the air quality sensor 100 is emplaced in the cabin 12 (shown in FIG. 1). In certain embodiments the 28-volt connector 118 is the sole source of power for the air quality sensor 100, the air quality sensor 100 being battery-less, simplifying certification requirements of the air quality sensor 100.

The PCB 102 connects the detector element array 104, the EEPROM 110, the processor 106, and the memory 108. In this respect the PCB 102 provides electrical communication between the processor 106, the detector element array 104, the EEPROM 110, and the memory 108. In certain embodiments the detector element array 104, the EEPROM 110, the processor 106, and the memory 108 are each supported by the PCB 102 and are arranged within an interior 118 of the enclosure 112 to provide a unitary arrangement. As will be appreciated, unitary arrangement facilitates reliability by rendering the air quality sensor 100 a line replaceable unit.

The relative humidity sensor 114 is connected to the PCB 102, and therethrough to the processor 106, and is configured to provide measurements of the relative humidity of the atmosphere 22 (shown in FIG. 1) to the processor 106. In certain embodiments the relative humidity sensor 114 can be external, e.g., remote, of the air quality sensor 100. In accordance with certain embodiments the relative humidity sensor 114 is arranged within the air quality sensor 100, providing accuracy of the air quality sensor 100 and limiting nuisance events.

The temperature sensor 116 is connected to the PCB 102, and therethrough to the processor 106, and is configured to provide measurements of the temperature of the atmosphere 22 (shown in FIG. 1) to the processor 106. In certain embodiments the temperature sensor 116 can be external, e.g., remote, of the air quality sensor 100. In accordance with certain embodiments the temperature sensor 116 is arranged within the air quality sensor 100, providing accuracy of the air quality sensor 100 and limiting nuisance events.

The enclosure 112 has an inlet 122. The inlet 122 is configured to provide fluid communication with the atmosphere 22 (shown in FIG. 1) contained within the cabin 12 (shown in FIG. 1) for flowing air from the atmosphere 22 across the detector element array 104. In certain embodiments the enclosure has a portable form factor 124, which allows the air quality sensor 100 to be hand-held and/or portable. In accordance with certain embodiments the enclosure 112 has a cabin-mountable form factor 126, which allows the air quality sensor 100 to be removably fixed within the cabin 12 (shown in FIG. 1) of the aircraft 10 (shown in FIG. 1).

Figure 3:
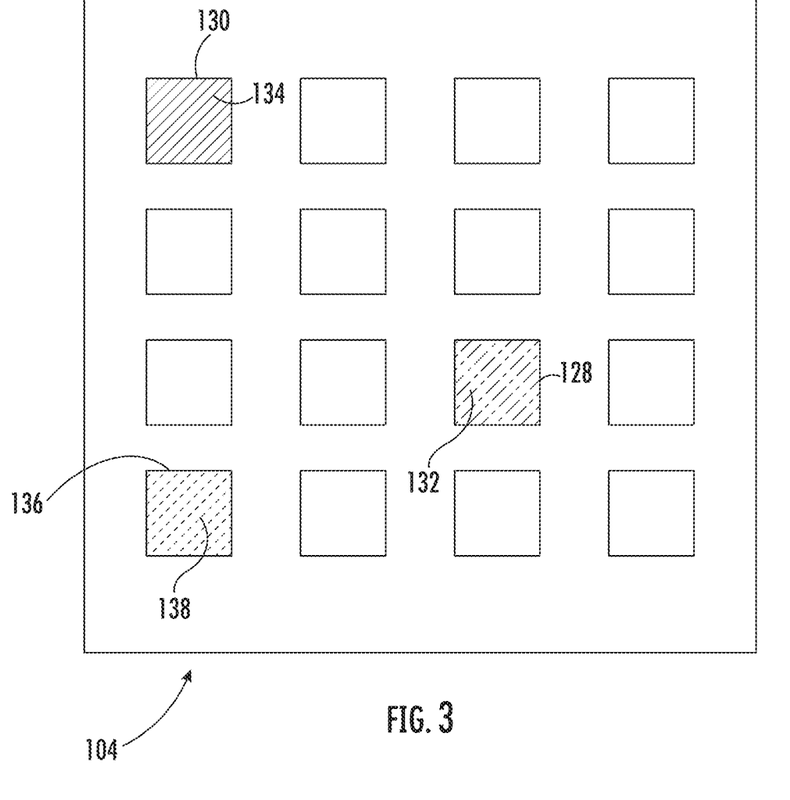
FIG. 3 is schematic view detector element array of the air quality sensor of FIG. 1, showing a plurality of detector elements for detecting contaminants and a negation sensor for detecting a spoof contaminant.

With reference to FIG. 3, the detector element array 104 is shown. The detector element array 104 includes a plurality of detector elements, e.g., a first detector element 128 and a second detector element 130. Two or more of the detector elements have chemiresistive coatings that differ from one another, e.g., the first detector element 128 having a first chemiresistive coating 132 and the second detector element 130 having a second chemiresistive coating 134. The first chemiresistive coating 132 is configured such that electrical resistance of the first detector element 128 changes upon contact with the nuisance contaminant 30 (shown in FIG. 1) differently, e.g., exhibits a larger change, than upon contact with the hazardous contaminant 32 (shown in FIG. 1). The second chemiresistive coating 134 is configured such that electrical resistance of the second chemiresistive coating 134 changes upon contact with the nuisance contaminant 30 differently, e.g., exhibits a larger change, than upon contact with the hazardous contaminant 32. Examples of suitable chemiresistive coatings include those shown and described in U.S. Pat. No. 8,683,672 B2 issued on Apr. 1, 2014 to Deshusses et al., the contents of which are incorporated herein by reference in its entirety.

In certain embodiments the detector element array 104 includes a plurality of nano-detector elements formed on a silicon substrate. As will be appreciated by those of skill in the art in view of the present disclosure, silicon substrates allow the fabrication of the detector elements and associated circuitry as a monolithic structure, simplifying the air quality sensor 100 (shown in FIG. 1). As shown in FIG. 1 the detector element array 104 includes sixteen (16) detector elements arranged in four (4) rows and four (4) columns. This is for illustration purposes only and is non-limiting as the air quality sensor 100 can have fewer than sixteen (16) detector elements or more than sixteen (16) detector elements, as suitable for an intended application.

In certain embodiments the detector element array 104 includes a negation detector element 136. The negation detector element 136 includes a negation chemiresistive coating 138 configured to change in electrical resistance with a spoof contaminant that also causes resistance change in another detector element of the detector element array 104, e.g., the first detector element 128 and the second detector element 130. This allows an algorithm resident on the air quality sensor 100 to employ chemiresistive coatings that change in resistance in response to exposure to more than one contaminant, allowing the air quality sensor 100 to employ, for example, certain tin-containing chemiresistive coatings.

With continuing reference to FIG. 2, the EEPROM 110 is connected to the PCB 102, is in electrical communication with the processor 106 through the PCB 102, and has recorded on a calibration data associated with the detector element array 104. In certain embodiments the calibration data provides the processor 106 with response characteristics of each of the plurality of detector elements for specific contaminants. In accordance with certain embodiments the calibration data includes relative humidity and/or temperature correction information for one or more the plurality of detector elements. As will be appreciated by those of skill in the art in view of the present disclosure, EEPROM 110 allows the air quality sensor 100 to be sensitized, for example with respect to contaminant concentration, to be suitable for the atmosphere 22 (shown in FIG. 1) of the aircraft 10 (shown in FIG. 1).

The processor 106 is operatively connected to a user interface 142, and is disposed in communication with a device interface 144 and the memory 108. Operative association with the user interface 142 allows the processor to provide indication of presence and/or absence of contaminant within the atmosphere 22 (shown in FIG. 1). In certain embodiments operative association with the user interface 142 also allows for receiving input from a user, such as a silence input by way of non-limiting example.

The device interface 144 allow the processor to communicate with other devices. For example, the device interface 144 can provide communication between the processor 106 and the relative humidity sensor 114 such that the processor receives measurements of the relative humidity of air 24 flowing across the detector element array 104. Alternatively (or additionally), the device interface 144 can provide communication between the processor 106 and the temperature sensor 116 such that the processor receives measurements of the temperature of air 24 flowing across the detector element array 104. It is also contemplated that the device interface 144 enable the processor to communicate with the EEPROM 110, the processor 106 thereby receiving calibration information and/or reference resistances from the EEPROM 110.

The memory 108 has a plurality of program modules 140 recorded on it that, when read by the processor 106, cause the processor 106 to execute the operations of a method 200 (shown in FIG. 4) of monitoring air quality in an aircraft cabin, e.g., the cabin 12, as will be described. In certain embodiments the processor 106 and the memory 108 are arranged within the enclosure 112 with the detector element array 104, the PCB 102, and EEPROM 110, the relative humidity sensor 114, and the temperature sensor 116. As will be appreciated by those of skill in the view the present disclosure, packaging the processor 106 and the memory 108 within the enclosure 112 the detector element array 104, the PCB 102, and EEPROM 110, the relative humidity sensor 114, and the temperature sensor 116 allows the air quality sensor 100 to be removed and/or replaced for service, e.g., for calibration, as required during service life of the air quality sensor 100.

Figure 4:
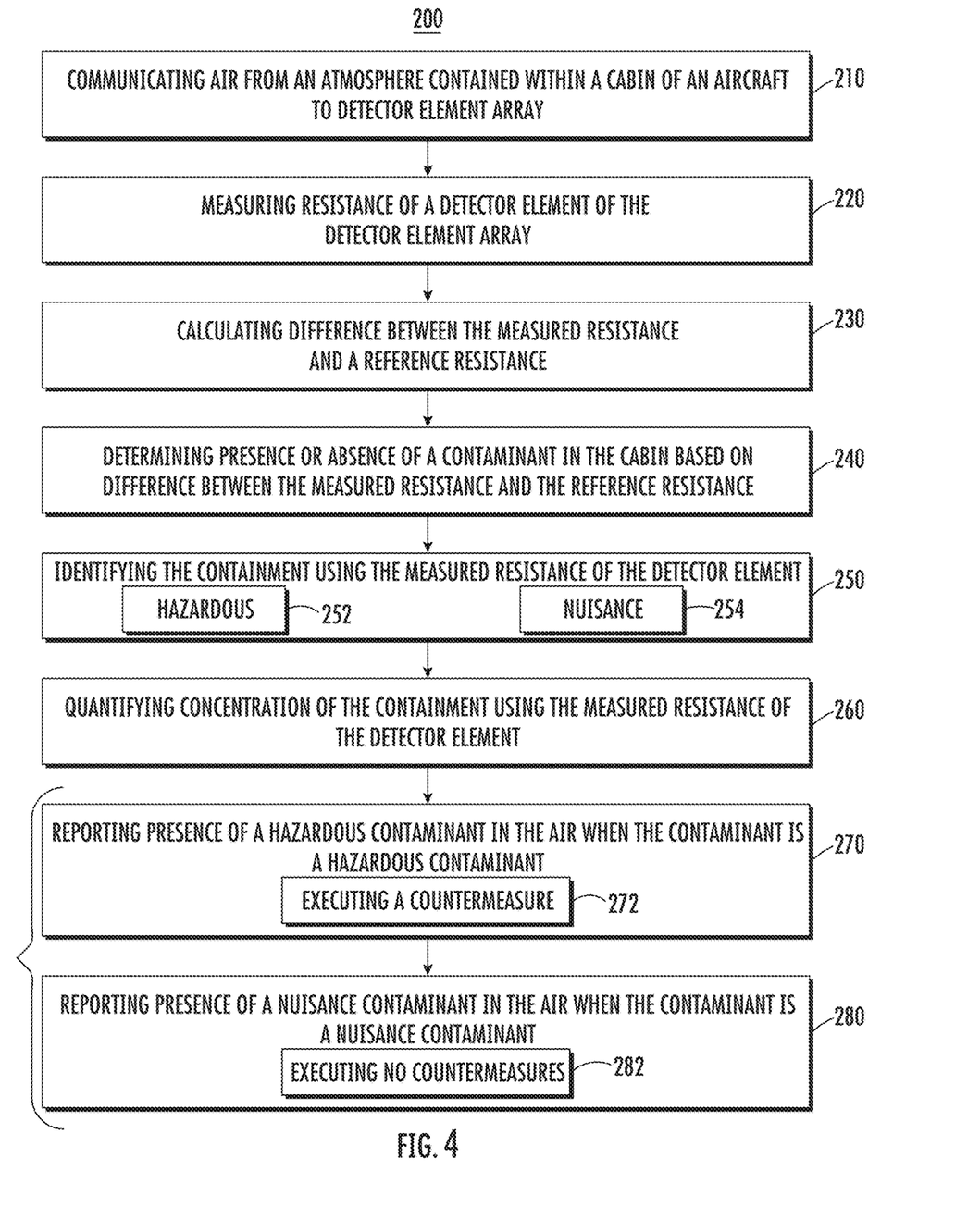
FIG. 4 is a block diagram of a method of air quality monitoring according to an embodiment of the present disclosure, showing operations of the method.

With reference to FIG. 4, the method 200 of monitoring air quality is shown. The method 200 includes communicating air from an atmosphere contained within a cabin of an aircraft to a detector element array, e.g., the air 24 (shown in FIG. 1) from the atmosphere 22 (shown in FIG. 1) contained within the cabin 12 (shown in FIG. 1), as shown with box 210. Resistance of a detector element of the detector element array, e.g., the first detector element 128 (shown in FIG. 3) and/or the second detector element 130 (shown in FIG. 3) of the detector element array 104 (shown in FIG. 2), as shown with box 220. It is contemplated that the air flowing across the detector element array selectively catalyze chemiresistive coatings, e.g., the first chemiresistive coating 132 (shown in FIG. 3) and/or the second chemiresistive coating 134 (shown in FIG. 3), thereby changing the resistance of one or more of the detector elements.

As shown with box 230, a difference is calculated between the measure resistance and a reference resistance. More specifically, for resistance is calculated for one or more of the detector elements of the detector element array and compared to the reference resistance for the detector element. The reference resistance can be retrieved, for example, from a lookup table recorded on either the EEPROM 110 (shown in FIG. 2) or from a program module resident on a memory, e.g., the program module 140 (shown in FIG. 2) on the memory 108 (shown in FIG. 2). In certain embodiments one of the measured resistance and the reference resistance can be relative humidity-compensated, e.g., adjusted using a relative humidity measurement provided by the relative humidity sensor 114 (shown in FIG. 2). In accordance with certain embodiments one of the measured resistance and the reference resistance can be temperature-compensated, e.g., adjusted using a temperature measurement provided by the temperature sensor 116 (shown in FIG. 2).

As shown with box 240, a determination of presence or absence of a contaminant, e.g., the hazardous contaminant 32 (shown in FIG. 1) or the nuisance contaminant 30 (shown in FIG. 1), is made based on the difference between the measured resistance and the reference resistance. In certain embodiments the hazardous contaminant and/or the nuisance contaminant present in the atmosphere can be identified, as shown with box 250. For example, a contaminant present in the atmosphere can be identified as hazardous, as shown with box 252. Alternatively (or additionally), a contaminant present in the atmosphere can be identified as a nuisance, as shown with box 254. It is also contemplated that the amount of one or more contaminant present within the atmosphere can be quantified, as shown with box 260.

As shown with box 270, presence of a hazardous contaminant in the atmosphere can be reported. For example, an indication can be provided to a user interface of the air quality sensor, e.g., the user interface 142, or to a remote interface that a hazardous contaminant is present in the atmosphere of the cabin during flight and in real-time with detection of the hazardous contaminant. Examples of remote interfaces include messaging devices located on the aircraft flight deck, electronic flight bag devices, and/or aircraft mobile devices. In certain embodiments the indication can include an advisement to aircrew and/or passengers to execute countermeasures, as shown with box 272. Examples of countermeasures include switching the source of makeup air provided to the cabin from one engine to another engine, such as by switching the makeup air 26 (shown in FIG. 1) from the first engine 18 (shown in FIG. 1) to the second engine 20 (shown in FIG. 1). The countermeasure can also include an instruction to divert the aircraft to another destination and/or route.

As shown with box 280, presence of a nuisance contaminant in the atmosphere can be reported. For example, an indication can be provided to the user interface of the air quality sensor indicating presence of a nuisance contaminant. It is also contemplated that an indication be provided instructing that no countermeasure need by taken in view of the recognition that a nuisance contaminant is present in the atmosphere of the cabin. Further, as shown be bracket 290, the method can include quantifying an amount of a nuisance contaminant and changing the associated indication when the quantity of the nuisance contaminant warrants designation of the contaminant as a hazardous contaminant.

Aircraft cabin air is typically not monitored for the presence of contaminants. On rare occasions a system malfunction may introduce fumes and/or odors into the cabin atmosphere. Since the system malfunction responsible for the fume and/or odor may not be readily discernible, it can be necessary to take the aircraft out of service to investigate the source of the fume and/or odor when present. When the source of the fumes and/or odors in the cabin atmosphere is a nuisance the outage associated with investigating the fumes and/or odors can unnecessarily inconvenience the aircrew and/or passengers of the aircraft.

In embodiments described herein an air quality sensor is provided. In certain embodiments the air quality sensor is mounted within the aircraft cabin to continuously monitor the cabin air quality. In accordance with certain embodiments, the air quality sensor includes a detector element array. It is contemplated that the detector element array can include chemiresistive nano-sensors sensitive to certain contaminants. It is also contemplated that the detector element array can include negation detector elements and/or negation algorithms to identify interferants, thereby preventing nuisance events from being mistaken as hazardous system malfunctions.

As described above, embodiments, such contaminant recognition algorithm described above, can be in the form of processor-implemented processes and devices for practicing those processes, such as a processor. Embodiments can also be in the form of computer program code containing instructions embodied in tangible media, such as network cloud storage, SD cards, flash drives, floppy diskettes, CD ROMs, hard drives, or any other computer-readable storage medium, wherein, when the computer program code is loaded into and executed by a computer, the computer becomes a device for practicing the embodiments. Embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into an executed by a computer, the computer becomes an device for practicing the embodiments. When implemented on a general-purpose microprocessor, the computer program code segments configure the microprocessor to create specific logic circuits.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. An aircraft, comprising:
an engine;
an environmental control system that receives makeup air from the engine;
a cabin containing an atmosphere from the environmental control system;
an air quality sensor, wherein the air quality sensor is exposed to the atmosphere contained within the cabin, the air quality sensor comprising:
a detector element array having at least two detector elements, including a first detector element and a second detector element; and
a processor operatively connected to the detector element array; and
a memory disposed in communication with the processor and having instructions recorded thereon that, when read by the processor, cause the processor to:
measure electrical resistance of one of more detector element of the detector element array;
calculate difference between the measured resistance and a reference resistance, and
determine at least one of a presence or absence of a contaminant in the air from the atmosphere of the cabin based on the difference between the measured resistance and the reference resistance;
wherein the instructions further cause the processor to identify the contaminant based on the difference between the measured resistance and the reference resistance; and wherein the instructions further cause the processor to distinguish the contaminant between a hazardous contaminant from the engine and a nuisance contaminant; and wherein the instructions further cause the processor to identify the specific contaminant from recorded calibration data associated with the detector element array;
wherein:
the first detector element has a first chemiresistive coating;
the second detector element has a second chemiresistive coating;
at least one of the first chemiresistive coating and the second chemiresistive coating catalyses in the presence of a hazardous contaminant from the engine;
at least one of the first chemiresistive coating and the second chemiresistive coating catalyses in the presence of a nuisance contaminant; and
the hazardous contaminant includes one or more of fire and smoke and the nuisance contaminant includes one or more of tobacco and fumes.

2. The aircraft as recited in claim 1, further comprising a user interface operatively associated with the processor, wherein the instructions cause the processor to provide a countermeasure required signal to the user interface.

3. The aircraft as recited in claim 1, further comprising a user interface operatively associated with the processor, wherein the instructions cause the processor to provide a no countermeasure required signal to the user interface.

4. The aircraft as recited in claim 1, further comprising an enclosure with an interior, wherein the detector element array is arranged within the interior of the enclosure.

5. The aircraft as recited in claim 4, wherein:
the enclosure includes an inlet into the interior; and
the air quality sensor includes:
a printed circuit board (PCB) arranged within the interior of the enclosure and supporting the detector element array; and
an electrical erasable programmable read only memory (EEPROM) arranged within the interior of the enclosure and supported by the PCB,
wherein the PCB connects the processor, the memory, and the EEPROM, for determining at least one of the presence or absence of contaminant with real-time measurements of resistivity change of detector elements of the detector element array.

6. A method of monitoring air quality, comprising:
exposing a detector element array having at least two detector elements, including a first detector element and a second detector element, to air from an atmosphere contained within a cabin of an aircraft;
measuring resistance of the first detector element of the detector element array, wherein the atmosphere is obtained from an environmental control system that receives makeup air from an aircraft engine;
calculating difference between the measured resistance and a reference resistance; and determining at least one of a presence or absence of a nuisance contaminant or a hazardous contaminant from the aircraft engine in the cabin based on difference between the measured resistance and the reference resistance;

wherein the measured resistance is a first measured resistance, and wherein the reference resistance is a first reference resistance, the method further comprising:

measuring resistance of the second detector element of the detector element array;

calculating difference between the measured resistance of the second detector element and a second reference resistance; and further comprising identifying specific contaminants using the measured resistances of the detector elements from recorded calibration data associated with the detector element array, wherein the hazardous contaminant includes one or more of fire and smoke and the nuisance contaminant includes one or more of tobacco and fumes.

7. The method as recited in claim 6, further comprising:
reporting presence of the hazardous contaminant in the air upon detecting the hazardous contaminant.

8. The method as recited in claim 6, further comprising quantifying concentration of the contaminant using the measured resistance of the detector element.

9. The method as recited in claim 6, further comprising:
executing a countermeasure when the contaminant is identified as a hazardous contaminant; and
executing no countermeasure when the contaminant is identified as a nuisance contaminant.

10. The method as recited in claim 6,
the method further comprising:
negating the determining of the presence of the contaminant based on the difference between the first measured resistance and the first reference resistance.

11. The method as recited in claim 6, further comprising:
reporting presence of the nuisance contaminant in the air upon detecting the nuisance contaminant.

* * * * *